(12) United States Patent
Kobayashi et al.

(10) Patent No.: US 7,276,052 B2
(45) Date of Patent: Oct. 2, 2007

(54) MEDICAL ASPIRATOR

(75) Inventors: Susumu Kobayashi, Osaka (JP); Tomoyuki Tejima, Osaka (JP)

(73) Assignee: Nipro Corporation, Osaka (JP)

( * ) Notice: Subject to any disclaimer, the term of this patent is extended or adjusted under 35 U.S.C. 154(b) by 183 days.

(21) Appl. No.: 10/757,567

(22) Filed: Jan. 15, 2004

(65) Prior Publication Data

US 2005/0159716 A1    Jul. 21, 2005

(51) Int. Cl.
*A61M 1/00* (2006.01)
*A61M 27/00* (2006.01)

(52) U.S. Cl. ..................... 604/319; 604/317
(58) Field of Classification Search ........ 604/319–320, 604/317
See application file for complete search history.

(56) References Cited

U.S. PATENT DOCUMENTS

| | | | | |
|---|---|---|---|---|
| 3,599,639 A | * | 8/1971 | Spotz | 604/119 |
| 3,885,567 A | * | 5/1975 | Ross | 604/120 |
| 3,982,540 A | * | 9/1976 | Ross | 604/540 |
| 4,147,478 A | * | 4/1979 | Vork | 417/458 |
| 4,188,196 A | * | 2/1980 | Casper et al. | 96/117.5 |
| 4,548,550 A | * | 10/1985 | Tsuji | 417/390 |
| 4,740,202 A | * | 4/1988 | Stacey et al. | 604/119 |
| 4,857,063 A | * | 8/1989 | Glenn | 604/317 |
| 5,419,768 A | * | 5/1995 | Kayser | 604/119 |
| 5,933,703 A | * | 8/1999 | Robertson | 428/549 |
| 6,383,163 B1 | * | 5/2002 | Kelly et al. | 604/74 |
| 6,764,462 B2 | * | 7/2004 | Risk et al. | 604/67 |
| 6,800,074 B2 | * | 10/2004 | Henley et al. | 604/319 |
| 2002/0198504 A1 | * | 12/2002 | Risk et al. | 604/318 |

OTHER PUBLICATIONS

"Nipro sells a thrombus suction system 'Nipro TVAC System'", *Nikkan Yakugyo Shimbun*, Jan. 15, 2003.
"Aspirate a Thrombus in Coronary Arteries", *Nikkan Kogyo Shimbun* "Business & Technology", Jan. 15, 2003.
"NIPRO sells a thrombus suction system", *Nikkan Iyaku Tokushin*, Jan. 15, 2003.

* cited by examiner

*Primary Examiner*—Tatyana Zalukaeva
*Assistant Examiner*—Keshia Gibson
(74) *Attorney, Agent, or Firm*—Kubovcik & Kubovcik

(57) ABSTRACT

A medical aspirator including an aspiration port, a reciprocating type electric pump for performing vacuum aspiration, a ventilation path which connects the aspiration port and the electric pump, an exhaust port, and an atmospheric pressure obtaining release valve for releasing a negative pressure in the ventilation path to obtain atmospheric pressure therein. The medical aspirator is particularly useful for percutaneous thrombus removal operation. A diaphragm pump is used as the electric pump. An electromagnetic valve is used as the atmospheric pressure obtaining release valve. The atmospheric pressure obtaining release valve is opened and closed in association with stopping and starting of the electric pump. A cell is provided as an internal power supply.

7 Claims, 3 Drawing Sheets

MEDICAL ASPIRATOR

BACKGROUND OF THE INVENTION

1. Field of the Invention

The present invention relates to a medical aspirator for aspirating, for example, thrombus, phlegm, and a body fluid such as blood.

2. Related Background Art

Conventionally, medical aspirators have been used in wide fields such as intraoral treatment for a patient at home or a patient in a hospital and aspiration of a body fluid such as blood at the time of a surgical operation.

However, these medical aspirators have a significant problem in that they are inferior in portability.

First, a first point concerning the problem of portability will be hereinafter described.

In general, in a medical aspirator, a reciprocating type electric pump has a larger startup load compared with a rotary electric pump. This is because startup energy loss of a mechanism for converting a rotational movement into a reciprocating movement is large. Therefore, special attention should be paid to the medical aspirator so that a sufficient startup property can be obtained in the medical aspirator that employs a reciprocating type electric pump.

Incidentally, in a diaphragm pump, which is one of the reciprocating type electric pumps, a pump mechanism section and a pump chamber are completely shielded and separated by a film. Thus, the diaphragm pump has a characteristic that contamination through the pump chamber is extremely little. Consequently, the diaphragm pump is widely used for various medical instruments. However, in a case in which the pump is stopped, since a negative pressure in the shut-off pump chamber is maintained, a restarting load increases. Thus, it is particularly hard to restart a diaphragm pump.

This problem is particularly conspicuous in portable or mobile medical instruments, medical instruments for surgical operations, or the like. In the portable or mobile medical instruments, various cells are used as a power supply. However, cells as small and light as possible are used for convenience of carrying. Thus, it is difficult to obtain a sufficient output overcoming a high load at the time of restart. In addition, in the medical instruments for surgical operations, in order to avoid contamination in a human body, a portion from a pump chamber to a body insertion part should be completely closed. In addition, during progress of an operation, emergency stopping or restarting may be required. Thus, reliability of restart is a significant issue involving life or death for a patient.

Currently, medical aspirators are used in a wide variety of fields such as intraoral treatment for a patient at home or a patient in hospital and aspiration of the body fluid such as blood at the time of a surgical operation. In addition, in recent years, medical aspirators have frequently been used for a percutaneous thrombus removal operation with a catheter being inserted in a coronary artery to aspirate thrombus.

In a conventional commercially available aspirator for a percutaneous thrombus removal operation, restart after emergency stop is performed by temporarily removing a coupling tube, which connects an aspirate sampling bottle and an aspiration port, from the aspiration port to open the aspirator to provide atmospheric pressure in the aspirator and then connecting the coupling tube to the aspiration port again to turn on a power supply.

However, it takes a lot of time and labor to perform these manipulations during an operation requiring urgency. In addition, since the coupling tube is connected to the aspiration port, which has a complicated shape, there is the likelihood of air leakage due to a connection failure or contamination of the aspirator via bloodstained gloves, which may result in spreading of a disease to other patients.

Next, a second point concerning the problem of portability will be hereinafter described.

At the time of aspirating a body fluid or the like, in particular, aspirating a coronary artery thrombus which is a cause of myocardial infarction, clogging frequently occurs in an aspiration catheter due to the thrombus during thrombus aspiration. In the present situation, an operator checks the clogging in the aspiration catheter by monitoring movement of an aspirate (blood) in the aspiration catheter or an aspiration tube, or in an aspirate sampling bottle. However, this monitoring work is a significant burden for the operator who is manipulating a catheter in a blood vessel for acute myocardial infarction which requires urgency. Thus, the clogging due to thrombus leads not only to a decrease in aspiration efficiency but also to a decrease in safety for a patient. In the worst case, the clogging is an issue of life and death for a patient.

This problem is conspicuous in a medical aspirator including an electric pump for vacuum aspiration or a medical aspirator including an internal power supply such as a cell. In other words, since importance is attached to portability in both the aspirators, a compact pump with less power consumption or a cell with relatively small capacity is inevitably selected. Consequently, there is not much margin in an aspiration force, and clogging of thrombus or the like particularly easily occurs.

SUMMARY OF THE INVENTION

Therefore, in order to solve the problem of inferior portability, the inventor concentrated his energy on providing a medical aspirator excellent in portability which can reliably and easily be restarted after an emergency stop and is hardly contaminated and is unlikely to cause infection, and which eliminates visual confirmation by an operator of clogging in an aspiration catheter or an aspiration tube to thereby reduce a burden on the operator and ensure safety of a patient and improvement of aspiration efficiency. As a consequence, the inventors have devised the present invention.

A feature of the present invention resides in that a medical aspirator for aspirating thrombus, phlegm, and a body fluid such as blood, includes: an aspiration port; a reciprocating type electric pump for performing vacuum aspiration; a ventilation path which connects the aspiration port and the electric pump; an exhaust port; and an atmospheric pressure obtaining release valve for releasing a negative pressure in the ventilation path to provide atmospheric pressure in the ventilation path.

Another feature of the present invention resides in that a diaphragm pump is used as the electric pump of the medical aspirator.

Further, another feature of the present invention resides in that an electromagnetic valve is used as the atmospheric pressure obtaining release valve of the medical aspirator.

Further, another feature of the present invention resides in that the atmospheric pressure obtaining release valve of the medical aspirator opens simultaneously with stopping of the electric pump and closes simultaneously with starting of the electric pump.

Further, another feature of the present invention resides in that a medical aspirator for aspirating thrombus, phlegm, and a body fluid such as blood, includes a clogging detection means which detects clogging in an aspiration tube or an aspiration catheter during an aspiration operation.

Further, still another feature of the present invention resides in that the medical aspirator is useful for a percutaneous thrombus removal operation.

Further, yet another feature of the present invention resides in that the medical aspirator includes clogging detection means for measuring a change in a flow rate of an aspirate.

Alternatively, another feature of the present invention resides in that the medical aspirator includes clogging detection means for measuring a change in a weight of an aspirate sampling bottle.

Alternatively, another feature of the present invention resides in that the medical aspirator includes clogging detection means for measuring a change in an amount of aspiration dropping in an aspirate sampling bottle.

Furthermore, another feature of the present invention resides in that the medical aspirator further includes clogging warning means for informing an operator that clogging in the aspiration tube or the aspiration catheter has occurred.

Furthermore, another feature of the present invention resides in that the medical aspirator further includes: fixing means for fixing an aspirate sampling bottle in a position for aspiration; and bottle illumination means for illuminating the inside of the aspirate sampling bottle.

Further, another feature of the present invention resides in that the medical aspirator further includes a cell for a power supply.

According to the medical aspirator in accordance with the present invention, since an atmospheric pressure obtaining release valve is provided in a primary side ventilation path of the electronic pump for performing vacuum aspiration, the inside of the pump chamber can be easily returned to atmospheric pressure by opening this atmospheric pressure obtaining release valve when aspiration is stopped. Consequently, a load at the startup time of the electric pump is reduced, and the electric pump can be restarted reliably.

In addition, the conventional work including the removal of the coupling tube from the aspirator in order to return the inside of the pump chamber to atmospheric pressure can be eliminated. Thus, for example, in the case in which the medical aspirator is used for a surgical operation, since time and labor are reduced, safety of the operation is improved, and infection to a patient via contamination of the medical aspirator is prevented.

In particular, in the medical aspirator for a percutaneous thrombus removal operation which exceptionally requires safety, the effect that the electric pump is reliably restarted becomes more conspicuous.

In particular, in the medical aspirator using a diaphragm with a large startup load, the effect that the electric pump is reliably restarted becomes extremely conspicuous.

In particular, since the electromagnetic valve is used as the atmospheric pressure obtaining release valve, manipulation for opening and closing the atmospheric pressure obtaining release valve is simplified, and association of the atmospheric pressure obtaining release valve with the power supply is facilitated.

In particular, since the atmospheric pressure obtaining release valve is adapted to open simultaneously with stopping of the electric pump and to close simultaneously with starting of the electric pump, stopping or restarting of aspiration can be performed only by one manipulation of turning the power supply switch on or off, which is very convenient.

In particular, since the fixing means for fixing the aspirate sampling bottle in a position for aspiration and the bottle illumination means for illuminating the inside of the aspirate sampling bottle are provided, a state of clogging of an aspirate can be visually recognized even in a poorly lighted place such as a darkroom or a corner of an operating room.

In particular, since the cell for a power supply is provided in the inside of the medical aspirator, congestion in a place of use can be avoided by eliminating a cord for the power supply. In addition, the medical aspirator can be moved and used anywhere regardless of whether it is outdoors or indoors, and the present invention can exceptionally improve poor restarting of the electric pump caused by adopting a cell with a small output.

Moreover, according to the medical aspirator in accordance with the present invention, since clogging in the aspiration catheter or the aspiration tube is automatically detected, visual recognition of a state of aspiration by an operator becomes unnecessary, and burden on the operator is reduced significantly. Further, since the operator can engage in other necessary duties comfortably, safety of an operation and a patient is remarkably improved.

This effect is particularly conspicuous in the medical aspirator for a percutaneous thrombus removal operation of great urgency in which clogging in the aspiration catheter tends to frequently occur.

In particular, this effect is exceptionally shown in the medical aspirator including the electric pump for vacuum aspiration and an internal power supply with less margin of an aspiration force.

Further, since the clogging detection means, which measures a change in a flow rate of an aspirate, a change in a weight of the aspirate sampling bottle, a change in an amount of aspirate dropping to the aspirate sampling bottle, or the like, clogging in the aspiration catheter or the aspiration tube can be detected more reliably.

In particular, since the clogging warning means such as a warning sound or a warning lamp is provided, occurrence of clogging in the aspiration catheter or the aspiration tube can be immediately notified to an operator, and treatment for a patient, treatment for restarting of aspiration, or the like can be promptly performed.

DETAILED DESCRIPTION OF THE PREFERRED EMBODIMENTS

Next, embodiments of the medical aspirator in accordance with the present invention will be described in detail with reference to the accompanying drawings.

First Embodiment

Figure 1:
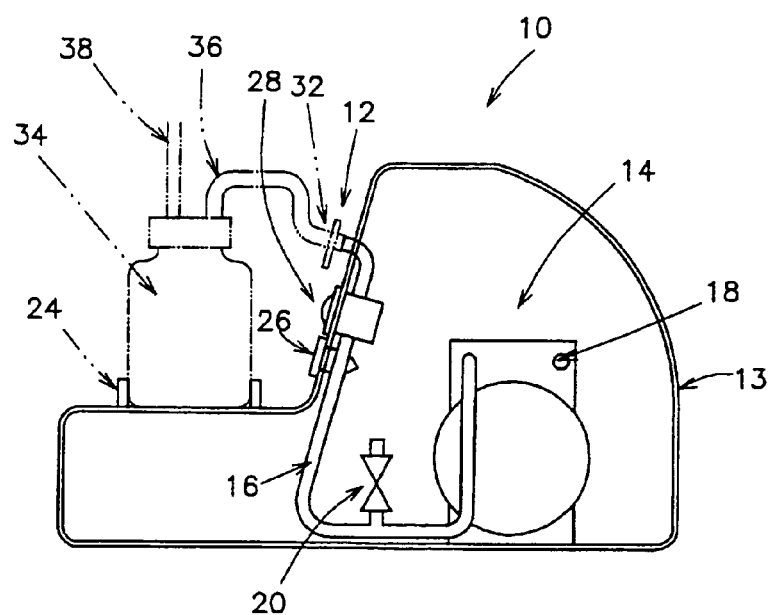
FIG. 1 is a longitudinal sectional view showing an example of a medical aspirator in accordance with a first embodiment of the present invention and schematically illustrating a main part thereof.
Figure 2:
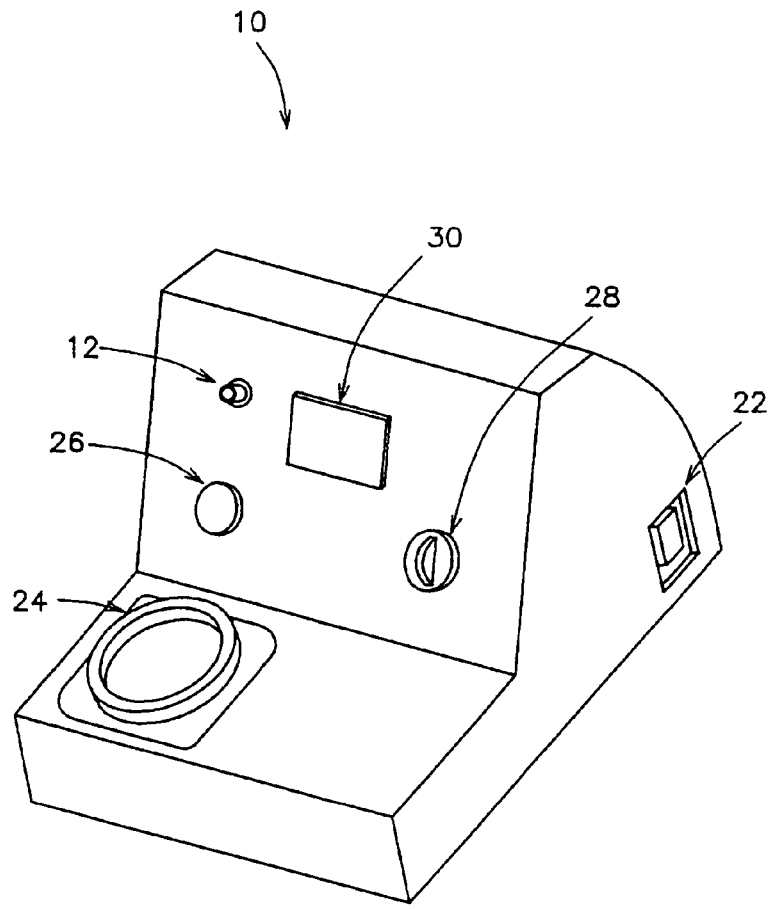
FIG. 2 is an external perspective view of the medical aspirator shown in FIG. 1 in accordance with the first embodiment of the present invention.

FIGS. 1 and 2 show a particularly preferred embodiment of the medical aspirator in accordance with the present invention. FIG. 1 is a longitudinal sectional view schematically showing a main part of the medical aspirator, and FIG. 2 is an external perspective view thereof. A medical aspirator 10 includes an aspiration port 12, a reciprocating type electric pump 14 for performing vacuum aspiration, a ventilation path 16 for connecting the aspiration port 12 and the electric pump 14, and an exhaust port 18. An atmospheric pressure obtaining release valve 20 for releasing a negative pressure in the ventilation path 16 to obtain atmospheric pressure therein, is provided in a position branched from the ventilation path 16.

In addition, the medical aspirator 10 also includes annular bottle fixing means 24, which projects in the shape of a base in a lower front part of the medical aspirator 10 and forms a place for putting an aspirate sampling bottle 34 thereon, and which is used for holding the lower circumference of the aspirate sampling bottle 34 to fix the same. Further, bottle illumination means 26 is provided in an upper front part of a body case 13 so as to face the fixing position (bottle fixing means 24) of the aspirate sampling bottle 34.

Moreover, adjustment means (not shown) for an aspiration pressure is provided in the medical aspirator 10. Thus, a pressure adjustment dial 28 for adjustment of an aspiration pressure and a pressure indicator 30 are also provided in the upper front part of the body case 13, and a power supply switch 22 is provided on the side of the body case 13.

The medical aspirator 10 is used as described below. First, the aspirate sampling bottle 34 in an aspiration catheter set composed of the aspirate sampling bottle 34, an aspiration tube 38, an aspiration catheter (not shown), and a coupling tube 36, is fitted in the annular bottle fixing means 24 provided in the lower front part of the aspirator and is coupled to the aspiration port 12 via the coupling tube 36. A filter 32 for preventing an aspirate from entering the electric pump 14 and, at the same time, preventing bacteria from entering the aspiration catheter is provided between the coupling tube 36 and the aspiration port 12. Preparation of the aspiration catheter is performed, and the power supply switch 22 is pressed to start the electric pump 14.

When the electric pump 14 is started, a pressure in a portion up to the tip of the aspiration tube 38 or the tip of the aspiration catheter connected to the aspiration tube 38 changes to a negative pressure through an aspiration route composed of the ventilation path 16, the aspiration port 12, the coupling tube 36, the aspirate sampling bottle 34, the aspiration tube 38, and the like. Thus, thrombus, phlegm, mucus, and a body fluid such as blood are aspirated. Then, the aspirate falls into the aspirate sampling bottle 34 and is sampled.

In the medical aspirator 10 of this embodiment, the atmospheric pressure obtaining release valve 20 is adapted to open simultaneously with stopping of the electric pump 14 and to close simultaneously with starting of the electric pump 14. Therefore, simultaneously with turning the power supply switch 22 off and stopping the electric pump 14, the atmospheric pressure obtaining release valve 20 opens, and pressure inside the ventilation path 16 is released to provide the atmospheric pressure. A pressure inside a pump chamber (not shown) in the electric pump 14, which communicates with the ventilation path 16, also changes to atmospheric pressure immediately.

Since the pressure inside the pump chamber returns to atmospheric pressure and the load at the start time is reduced in this way, the electric pump 14 can be easily restarted by turning the power supply switch 22 on. Then, since the atmospheric pressure obtaining release valve 20 closes simultaneously with the starting of the electric pump 14, pressure in the aspiration route promptly changes to negative, and aspiration is started.

As in this embodiment, if the atmospheric pressure obtaining release valve 20 is adapted to be associated with the electric pump 14, stopping and restarting of aspiration can be performed by one manipulation of only turning the power supply switch 22 on or off, which is very convenient. However, the present invention may be carried out by separately operating the atmospheric pressure obtaining release valve 20 and the electric pump 14. In other words, an opening and closing switch of the atmospheric pressure obtaining release valve 20 is provided separately from the power supply switch 22 such that this opening and closing switch can be operated independently. When aspiration is stopped temporarily, the atmospheric pressure obtaining release valve 20 is opened while the electric pump 14 is kept operating to return the pressure inside the aspiration route to a substantial atmospheric pressure and to stop the aspiration. In restarting the aspiration, the atmospheric pressure obtaining release valve 20 only has to be closed. An aspiration pressure is transmitted in a pulse-like manner by repeatedly performing this manipulation in a short period of time. This is considered to be an effective method as a measure to cope with clogging in the aspiration catheter. However, before the atmospheric pressure obtaining release valve 20 is used, it is necessary to block the aspiration route by means for blocking the aspiration tube 38 such as a clamp, which is attached to the aspiration tube 38 side, to prevent a backward flow of the aspirate in advance.

A type and a structure of the atmospheric pressure obtaining release valve 20 are not specifically limited. The atmospheric pressure obtaining release valve 20 may be a mechanical valve which is mainly opened and closed manually or may be an electric valve which is opened and closed by an electric force. An electric valve can be opened and closed by manipulation of a switch and is very convenient. The electric valve can be easily associated with the electric pump 14 through a circuit contrivance and can be provided with a common switch. An electric valve which is opened and closed by the drive of a motor can also be used. However, an electromagnetic valve which can be miniaturized is preferable, and above all, a direct-acting electromagnetic valve is particularly preferably used.

The electric pump 14 is of a reciprocating type. Examples of the electric pump 14 include various types of pumps such as a piston pump, a plunger pump, and a wing pump. In particular, a diaphragm pump is preferably used. The diaphragm pump has a characteristic that a pump chamber is not easily contaminated, the diaphragm pump is relatively compact and light, has a long durable life, and consumes less power. In the diaphragm pump, one side of a pump chamber is constituted by an elastic film made of rubber or plastics, and this elastic film is moved by increasing or decreasing a pressure of air or an amount of liquid from its back or is moved mechanically or electrically. Consequently, a volume of the pump chamber is increased or decreased to suck liquid from an inlet and discharge it from an outlet by valve mechanisms provided in the inlet and the outlet. As the diaphragm pump, there are a single acting type pump provided with one pump chamber and a double acting type pump provided with two pump chambers on both sides of a reciprocating lever. The single acting type pump has a characteristic that, although suction is intermittent, the pump can be easily miniaturized. On the other hand, the double acting type pump has a characteristic that suction is averaged. The diaphragm pump is selected from these two types so as to make use of their particular characteristics.

The medical aspirator 10 includes bottle fixing means 24 for fixing the aspirate sampling bottle 34 in position for aspiration and bottle illumination means 26 for illuminating the inside of the aspirate sampling bottle 34. For example, during an aspiration operation for removal of thrombus, an operator judges the presence or absence of thrombus clogging the aspiration catheter or the aspiration tube 38 based on a flow rate of the aspirate in the aspirate sampling bottle 34. Thus, it is preferable to include the bottle illumination means 26 such that the flow rate of the aspirate in the aspirate sampling bottle 34 can be confirmed when the medical aspirator 10 is used in a catheter room of a darkroom state or in a poorly lighted place such as a corner of an operating room. It is also preferable to include the bottle fixing means 24 for fixing the aspirate sampling bottle 34 in a position facing the bottle illumination means 26 such that the aspirate sampling bottle 34 is easily observed at any time.

The bottle illumination means 26 is provided so as not to project from the aspirator such that it does not come into contact with the aspirate sampling bottle 34 or the like so as to be damaged. It is preferable to provide a cover for protection. In addition, as a lamp for illumination, a halogen lamp, an LED, or the like with relatively high luminance is preferably used.

The bottle fixing means 24 may be any fixing means as long as it keeps the aspirate sampling bottle 34 stable in a fixed position, and is not specifically limited. However, the bottle fixing means 24 should not prevent observation of a dropping state of the aspirate. For example, the bottle fixing means 24 is constituted using annular fixing means which is formed such that the lower part of the aspirate sampling bottle 34 fits therein as shown in FIG. 2, several bar-like objects which are erected so as to surround the lower side of the aspirate sampling bottle 34, a clamp, or the like.

The medical aspirator 10 is also provided with aspiration pressure adjustment means. Aspiration pressure can be adjusted to a pressure suitable for treatment by manipulating the pressure adjustment dial 28 while looking at the pressure indicator 30, which is very convenient.

A power supply of the medical aspirator 10 may be an external power supply to be supplied via an electrical outlet or the like from the outside or may be an internal power supply such as a built-in cell. In general, since an extremely large number of cords are already scattered on the floor of an operating room or the catheter room, it is desirable to avoid further providing a cord for the power supply of the medical aspirator 10. If an internal power supply is adopted, since the cord for the power supply becomes unnecessary, this problem is solved. In addition, if the internal power supply is adopted, the medical aspirator 10 can be moved and used freely anywhere whether it is outdoors or indoors, which is very convenient.

The cell used as the internal power supply may be any cell, for example, a primary cell such as a manganese dry cell, a secondary cell such as a nickel-cadmium cell or a lithium-ion cell, or other battery. In any case, as long as a small and light cell is selected attaching importance to portability, since an excessive output cannot be expected of the electric pump 14, the issue of securing a restarting property is exceptionally important, and the effect of the present invention is shown conspicuously in this point.

The medical aspirator of the present invention is particularly effective in a percutaneous thrombus removal operation. The percutaneous thrombus removal operation is a heart operation for aspirating and removing thrombus via an aspiration catheter which is inserted into the chest from the femoral artery or the radial artery. Thus, depending upon a symptom of a patient, whereas it is necessary to urgently stop aspiration, rapid aspiration may be required again. In other words, in the percutaneous thrombus removal operation, if the electric pump 14 is not restarted reliably, life of the patient may be affected. Thus, the effect of the present invention that the power supply pump 14 is restarted reliably is given particularly high importance.

The medical aspirator in accordance with the present invention has been described in detail in conjunction with a first preferred embodiment. However, the present invention is not limited to the above-mentioned embodiment or illustration. The present invention can be carried out with the addition of various improvements, modifications, or alterations on the basis of the knowledge of those skilled in the art in a range not departing from the spirit of the present invention with respect to shape and structure of the medical aspirator, type of electric pump, the atmospheric pressure obtaining release valve, and the internal power supply, type and structure of the bottle fixing means and the bottle illumination means, and the like.

Second Embodiment

Figure 3:
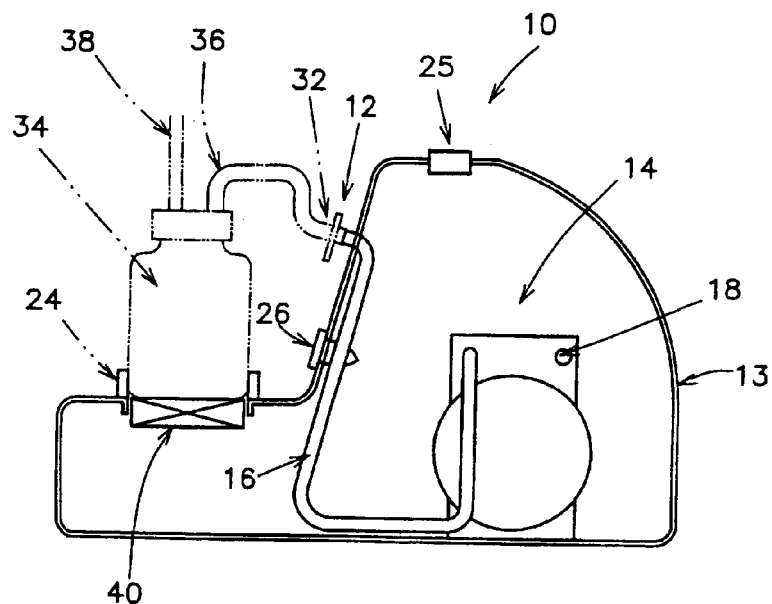
FIG. 3 is a longitudinal sectional view showing an example of a medical aspirator in accordance with a second embodiment of the present invention and schematically illustrating a main part thereof.
Figure 4:
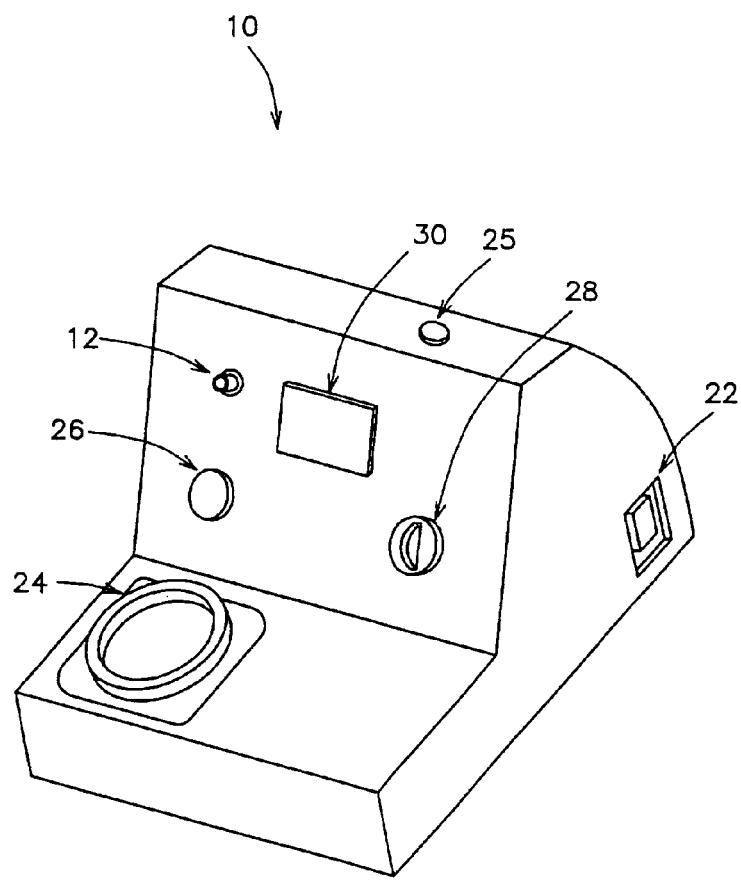
FIG. 4 is an external perspective view of the medical aspirator shown in FIG. 3 in accordance with the second embodiment of the present invention.

FIGS. 3 and 4 show a particularly preferred second embodiment of the medical aspirator in accordance with the present invention. FIG. 3 is a longitudinal sectional view schematically showing a main part of the medical aspirator, and FIG. 4 is an external perspective view thereof. A medical aspirator 10 includes an aspiration port 12, an electric pump 14 for performing vacuum aspiration, a ventilation path 16 for connecting the aspiration port 12 and the electric pump 14, and an exhaust port 18.

In addition, the medical aspirator 10 also includes annular bottle fixing means 24, which projects in the shape of a base in a lower front part of the medical aspirator 10 and forms a place for putting an aspirate sampling bottle 34 thereon, and which is used for holding the lower circumference of the aspirate sampling bottle 34 to fix the same. Further, bottle illumination means 26 is provided in an upper front part of a body case 13 so as to face the fixing position (bottle fixing means 24) of the aspirate sampling bottle 34.

In addition, a load cell (clogging detection means) 40 is disposed at the bottom of the fixed position (bottle fixing means 24) of the aspirate sampling bottle 34. A buzzer (clogging warning means) 25 is disposed at the top of the body case 13.

Moreover, adjustment means (not shown) for an aspiration pressure is provided in the medical aspirator 10. Thus, a pressure adjustment dial 28 for adjustment of aspiration pressure and a pressure indicator 30 are also provided in the upper front part of the body case 13, and a power supply switch 22 is provided on the side of the body case 13.

The medical aspirator 10 of the second embodiment is used as follows. First, the aspirate sampling bottle 34 in an aspiration catheter set composed of the aspirate sampling bottle 34, an aspiration tube 38, an aspiration catheter (not shown), and a coupling tube 36 is fitted in the annular bottle fixing means 24 provided in the lower front part of the aspirator and is coupled to the aspiration port 12 via the coupling tube 36. A filter 32 for preventing an aspirate from entering the electric pump 14 and, at the same time, preventing bacteria from entering the aspiration catheter is provided between the coupling tube 36 and the aspiration port 12. Preparation of the aspiration catheter is performed, and the power supply switch 22 is pressed to start the electric pump 14.

When the electric pump 14 is started, a pressure in a portion up to the tip of the aspiration tube 38 or the tip of the aspiration catheter connected to the aspiration tube 38 changes to a negative pressure through an aspiration route consisting of the ventilation path 16, the aspiration port 12, the coupling tube 36, the aspirate sampling bottle 34, the aspiration tube 38, and the like. Thus, thrombus, phlegm, mucus, and a body fluid such as blood can be aspirated. The aspirate falls into the aspirate sampling bottle 34 and is sampled.

The medical aspirator 10 of the second embodiment is provided with a load cell (clogging detection means) 40 for measuring the weight of the aspirate sampling bottle 34. When clogging in the aspiration catheter or the aspiration tube occurs, since aspiration efficiency of an aspirate such as blood decreases, a rate of increase in weight of the aspirate sampling bottle 34 decreases. Therefore, clogging in the aspiration catheter or the aspiration tube can be detected by measuring a change in weight of the aspirate sampling bottle 34 with the load cell 40. Then, if clogging is detected, a warning sound is immediately emitted by the buzzer (clogging warning means) 25 to inform an operator that the clogging has occurred.

The medical aspirator of the present invention is particularly effective in a percutaneous thrombus removal operation. In the percutaneous thrombus removal operation, thrombus is aspirated and removed via an aspiration catheter which is inserted into the chest from the femoral artery or the radial artery. However, since the aspiration catheter is oblong and the thrombus is often hard to flow, clogging easily occurs in the aspiration catheter. In addition, since the percutaneous thrombus removal operation is an operation for myocardial infarction or the like, which is carried out near the heart, affecting the life or death of a patient, an operator has to concentrate all of his/her nerves on the operation. It is a particularly heavy burden for the operator to visually monitor clogging of the aspiration catheter or the aspiration tube.

In addition, the present invention is particularly effective for the medical aspirator 10 including the electric pump 14 for vacuum aspiration. In such a medical aspirator 10, higher importance is attached to portability or mobility as compared with a medical aspirator relying upon an external aspiration source. Thus, a small electric pump 14 is inevitably used, and there is not a large margin in aspiration force, and clogging of thrombus or the like occurs particularly easily.

The electric pump 14 is not particularly limited. Examples of the electric pump 14 include a diaphragm pump, a piston pump, a vane type pump, and the like. In particular, a diaphragm pump is preferably used. In the diaphragm pump, one side of a pump chamber is constituted by an elastic film made of rubber or plastics, and this elastic film is moved by increasing or decreasing a pressure of air or an amount of liquid from its back or is moved mechanically or electrically. Consequently, a volume of the pump chamber is increased or decreased to suck liquid from an inlet and discharge it from an outlet by valve mechanisms provided in the inlet and the outlet. As the diaphragm pump, there are a single acting type pump provided with one pump chamber and a double acting type pump provided with two pump chambers on both sides of a reciprocating lever. The single acting type pump has a characteristic that, although suction is intermittent, the pump can be easily miniaturized. On the other hand, the double acting type pump has a characteristic that suction is averaged. The diaphragm pump is selected from these two types so as to make use of their particular characteristics.

A power supply of the medical aspirator 10 may be an external power supply to be supplied via an electrical outlet or the like from the outside or may be an internal power supply such as a built-in cell. In general, since an extremely large number of cords are already scattered on the floor of an operating room or catheter room, it is desirable to avoid further providing a cord for the power supply of the medical aspirator 10. If the internal power supply is adopted, since the cord for the power supply becomes unnecessary, this problem is solved. In addition, if the internal power supply is adopted, the medical aspirator 10 can be used anywhere even if it is outdoors, which is very convenient.

In addition, the present invention is particularly effective for the medical aspirator 10 including a cell for a power supply. In such a medical aspirator 10, higher importance is attached to portability or mobility as compared with a medical aspirator relying upon an external power source such as a commercial power source. Thus, a cell which is compact and light, and has a relatively small capacity is inevitably selected. Therefore, there is used an electric pump 14 which does not have much margin in aspiration force, and clogging of thrombus or the like can occur particularly easily.

The cell used as the internal power supply may be any cell, for example, a primary cell such as a manganese dry cell, a secondary cell such as a nickel-cadmium cell or a lithium-ion cell, or other battery. Among various kinds of electronic equipment and electronic parts included in the medical aspirator 10, the electric pump 14 has the highest load. Therefore, it is preferable to set the power source and voltage based on a voltage at which the electric pump 14 is used.

The medical aspirator 10 includes bottle fixing means 24 for fixing the aspirate sampling bottle 34 in position for aspiration and bottle illumination means 26 for illuminating the inside of the aspirate sampling bottle 34. The medical aspirator 10 automatically monitors a state of aspiration with the clogging detection means 40. However, it is necessary to visually confirm the state of aspiration occasionally looking at the aspirate sampling bottle 34, for example, at an initial aspiration condition setting time or aspirate observation time. Thus, it is preferable to also include the bottle illumination means 26 in a position facing the bottle fixing means 24 such that the aspirate sampling bottle 34 can be seen well even in a poorly lighted place such as a corner of an operating room or a catheter room.

The bottle illumination means 26 is provided so as not to project from the aspirator such that it does not come into contact with and damage the aspirate sampling bottle 34 or the like. It is preferable to provide a cover for protection. In addition, as a lamp for illumination, a halogen lamp, an LED, or the like with relatively high luminance is preferably used.

The bottle fixing means 24 may be any fixing means as long as it keeps the aspirate sampling bottle 34 stable in a fixed position, and is not specifically limited. However, the bottle fixing means 24 should not prevent observation of a dropping state of the aspirate. For example, the bottle fixing means 24 may be constituted using annular fixing means which is formed such that the lower part of the aspirate sampling bottle 34 fits therein as shown in FIG. 4, several bar-like objects which are erected so as to surround the lower side of the aspirate sampling bottle 34, a clamp, or the like.

The medical aspirator 10 is also provided with aspiration pressure adjustment means. This is very convenient because an operator can adjust an aspiration pressure to a pressure suitable for treatment by manipulating the pressure adjustment dial 28 while looking at the pressure indicator 30.

In the medical aspirator 10 illustrated in FIGS. 3 and 4, the clogging detection means is a load cell 40, which measures a change in a weight of the aspirate sampling bottle 34. The load cell includes means which is generally used as weight measurement means, and is also a preferable embodiment for the present invention.

However, the clogging detection means in the present invention is not specifically limited. In another particularly preferable embodiment, detection of clogging is performed by measuring a change in a flow rate of an aspirate such as blood in the aspiration catheter or the aspiration tube. For example, flow rate in a part of the aspiration tube 38 immediately before the aspirate sampling bottle 34 is continuously measured by an electromagnetic flowmeter, an ultrasonic wave flowmeter, or the like during an aspiration operation and, when the flow rate falls to a set value or less, it can be judged that clogging has occurred.

In addition, in another particularly preferable embodiment, detection of clogging is performed by counting the number of aspirate droppings into the aspirate sampling bottle 34. For example, the presence or absence of dropping is detected by a laser sensor or the like and, when a frequency of dropping falls to a set value or less, it can be judged that clogging has occurred.

Further, it is also possible to detect clogging based on a change in a pressure in the ventilation path 16. Since an aspiration pressure increases when the aspiration catheter or the aspiration tube is blocked, when the aspiration pressure rises to a set value or more, it can be judged that clogging has occurred. It is also possible to set a threshold value for an output to the pressure indicator 30 and emit a warning when the output increases to the threshold value or more. In any case, the set value and the threshold value for judging clogging should be variable.

When clogging in the aspiration catheter or the aspiration tube has occurred, it is preferable that an operator is informed to that effect immediately, and prompt measures for restart of aspiration are taken. In the medical aspirator 10 illustrated in FIGS. 3 and 4, a clogging warning means emitting a warning sound with a buzzer is adopted. Examples of the clogging warning means emitting a warning sound include, in addition to the buzzer, a bell, various electronic sounds, and artificial voices. The clogging warning means is not specifically limited. If the warning means using a warning sound is adopted, an operator can concentrate on manipulation sufficiently and safety of an operation or a patient is remarkably improved because it is unnecessary for the operator to look at the medical aspirator 10 in order to monitor clogging during the manipulation.

Another preferable embodiment of the clogging warning means is a warning lamp. An operator has to look at the warning lamp to confirm lighting or blinking thereof. However, since the confirmation is performed visually, the operator does not confuse the warning by the warning lamp with a large number of warning sounds in an operating room or a catheter room, and the operator is warned of the clogging reliably. As the warning lamp, various lamps, LEDs, or the like can be used.

Figure 5:
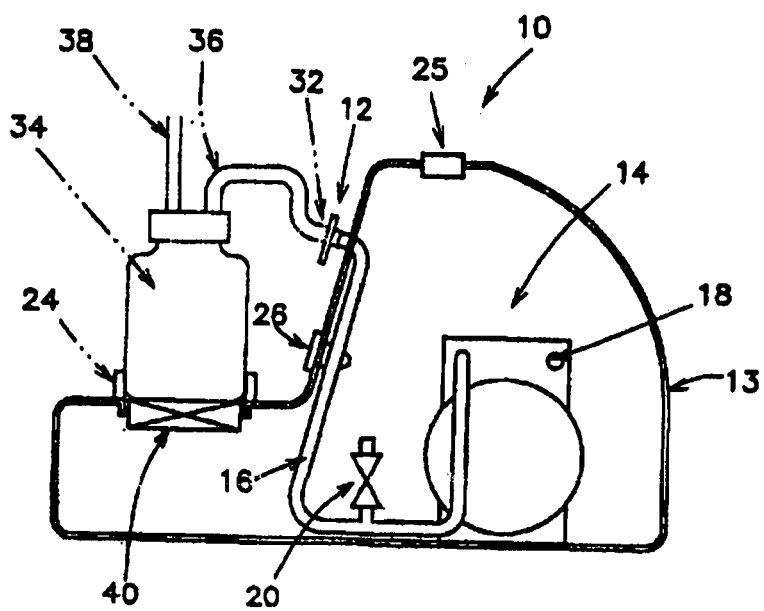
FIG. 5 is a longitudinal sectional view showing an example of a medical aspirator in accordance with the present invention which combines elements of the first and second embodiments of the present invention and schematically illustrating a main part thereof.
Figure 6:
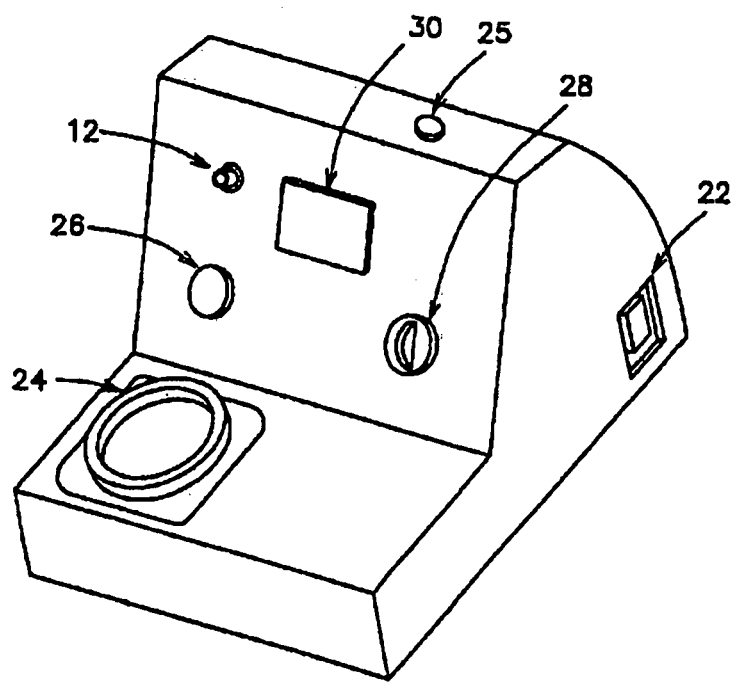
FIG. 6 is an external perspective view of the medical aspirator shown in FIG. 5.

The medical aspirator in accordance with the present invention has been described in detail in conjunction with a second preferred embodiment. However, the present invention is not limited to the above-mentioned embodiment or illustration. The present invention can be carried out with the addition of various improvements, modifications, or alterations on the basis of the knowledge of those skilled in the art in a range not departing from the spirit of the present invention with respect to shape and structure of the medical aspirator, type of the electric pump and internal power supply, type and structure of the clogging detection means, clogging warning means, bottle fixing means, bottle illumination means, and the like. Thus, for example, the medical aspirator in accordance with the present invention can be provided with both a clogging detection means as described in conjunction with the second preferred embodiment and an atmospheric pressure obtaining release valve as described in conjunction with the first preferred embodiment. Such an embodiment is shown in FIGS. 5 and 6 of the application.

What is claimed is:

1. A medical aspirator for aspirating thrombus, phlegm, or a body fluid such as blood, comprising:
    an aspiration port;
    a reciprocating type electric pump for performing vacuum aspiration;
    a ventilation path which connects the aspiration port and the electric pump;
    an exhaust port; and
    an atmospheric pressure obtaining release valve provided in the ventilation path for releasing a negative pressure in the ventilation path and providing atmospheric pressure in the ventilation path, the atmospheric pressure obtaining release valve being adapted to open simultaneously with stopping of the electric pump and to close simultaneously with starting of the electric pump.

2. A medical aspirator according to claim 1, wherein the electric pump is a diaphragm pump.

3. A medical aspirator according to claim 1, wherein the atmospheric pressure obtaining release valve is an electromagnetic valve.

4. A medical aspirator according to claim 2, wherein the atmospheric pressure obtaining release valve is an electromagnetic valve.

5. A medical aspirator according to claim 1, further comprising a clogging detection means which detects clogging in an aspiration catheter or an aspiration tube during an aspiration operation.

6. A medical aspirator according to claim 1, further comprising a cell for a power supply.

7. A medical aspirator for aspirating thrombus, phlegm, or a body fluid such as blood, comprising:
    an aspiration port;
    a reciprocating type electric pump for performing vacuum aspiration;
    a ventilation path connecting the aspiration port and the electric pump;

an exhaust port; and a clogging detection means which detects clogging in an aspiration catheter or an aspiration tube during an aspiration operation;

further comprising an atmospheric pressure obtaining release valve provided in the ventilation path for releasing a negative pressure in the ventilation path and providing atmospheric pressure in the ventilation path, the atmospheric pressure obtaining release valve being adapted to open simultaneously with stopping of the electric pump and to close simultaneously with starting of the electric pump.

* * * * *